(12) United States Patent
Flasinski et al.

(10) Patent No.: US 8,673,631 B2
(45) Date of Patent: Mar. 18, 2014

(54) CHIMERIC REGULATORY SEQUENCES COMPRISING INTRONS FOR PLANT GENE EXPRESSION

(75) Inventors: Stanislaw Flasinski, Chesterfield, MO (US); Christopher Hubmeier, Ballwin, MO (US); Maolong Lu, St. Louis, MO (US); Marianne Malven, Ellisville, MO (US); Wei Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/280,227

(22) Filed: Oct. 24, 2011

(65) Prior Publication Data
US 2012/0131694 A1   May 24, 2012

Related U.S. Application Data

(62) Division of application No. 11/706,684, filed on Feb. 15, 2007, now abandoned.

(60) Provisional application No. 60/774,700, filed on Feb. 17, 2006.

(51) Int. Cl.
*C07H 21/04*   (2006.01)
*C12N 15/00*   (2006.01)
*C12N 15/63*   (2006.01)
*A01H 1/00*    (2006.01)

(52) U.S. Cl.
USPC ......... 435/320.1; 435/6.1; 435/468; 435/410; 435/419; 536/24.1; 800/278; 800/295

(58) Field of Classification Search
USPC .......... 435/6, 468, 410, 419, 320.1; 536/24.1; 800/278, 295
See application file for complete search history.

(56) References Cited

U.S. PATENT DOCUMENTS

| | | | | |
|---|---|---|---|---|
| 5,684,239 | A | 11/1997 | Wu et al. | 800/205 |
| 5,830,477 | A | 11/1998 | Lathe et al. | 424/224.1 |
| 5,955,650 | A | 9/1999 | Hitz et al. | 800/281 |
| 6,166,302 | A | 12/2000 | Merlo et al. | 800/320.1 |
| 6,660,911 | B2 | 12/2003 | Fincher et al. | 800/300 |
| 6,919,495 | B2 | 7/2005 | Fincher et al. | 800/300 |
| 2003/0188346 | A1* | 10/2003 | Baerson et al. | 800/300 |
| 2005/0005333 | A1* | 1/2005 | Ruezinsky et al. | 800/281 |
| 2005/0108786 | A1* | 5/2005 | Heck et al. | 800/278 |
| 2007/0204367 | A1 | 8/2007 | Flasinski et al. | 800/278 |
| 2010/0275326 | A1 | 10/2010 | Dasgupta et al. | |

FOREIGN PATENT DOCUMENTS

| WO | WO 01/44457 | 6/2001 |
|---|---|---|
| WO | WO 2006/094976 | 9/2006 |

OTHER PUBLICATIONS

Brazas et al., "Identification and purification of a protein that binds DNA cooperatively with the yeaset SWI5 protein," *Mol. & Cell. Biol.*, 13(9):5524-5537, 1993.
Callis et al., "Introns increase gene expression in cultured maize cells," *Genes & Dev.*, 1:1183-1200, 1987.
Chaubet et al., "Identification of cis-elements regulating the expression of an *Arabidopsis* histone H4 gene," *Plant Journal*, 10(3):425-435, 1996.
Christensen et al., "Maize polyubiquitin genes: structure, thermal perturbation of expression and transcript splicing, and promoter activity following transfer to protoplasts by electroporation," *Plant Mol. Biol.*, 18(4):675-689, 1992.
Christensen et al., "Ubiquitin promoter-based vectors for high-level expression of selectable and/or screenable marker genes in monocotyledonous plants," *Transgenic Res.*, 5(3):213-218, 1996.
Clancy et al., "Maize shrunken1 intron and exon regions increase gene expression in maize protoplasts," *Plant Sci.*, 98:151-161, 1994.
Dennis et al., "Molecular analysis of the alcohol dehydrogenase (Adh1) gene of maize," *Nucleic Acids Res.*, 12(9):3983-4000, 1984.
GenBank Database Accession No. L04967, Jul. 22, 1997.
Gidekel et al., "The first intron of the *Arabidopsis thaliana* gene coding for elongation factor 1β contains an enhancer-like element," *Gene*, 170:201-206, 1996.
Hatton, et al., "Two classes of cis sequences contribute to tissue-specific expression of a PAL2 promoter in transgenic tobacco," *Plant Journal*, 7(6):859-876, 1995.
Jeong et al., "Distinct roles of the first introns on the expression of *Arabidopsis* profilin gene family members," *Plant Physiology*, 140:196-206, 2006.
Last et al., "pEmu: an improved promoter for gene expression in cereal cells," *Theoretical and Applied Genetics*, 81(5):581-588, 1991.
Luehrsen et al., "Addition of A- and U-rich sequence increases the splicing efficiency of a deleted form of a maize intron," *Plant Mol. Biol.*, 24(3):449-463, 1994.
Luehrsen et al., "Intron enhancement of gene expression and the splicing efficiency of introns in maize cells," *Mol. Gen. Genet.*, 225:81-93, 1991.
Maas et al, "The combination of a novel stimulatory element in the first exon of the maize shrunken-1 gene with the following intron 1 enhances reporter gene activity expression up to 1000-fold," *Plant Mol. Biol.*, 16:199-207, 1991.
Mascarenhas et al., "Intron-mediated enhancement of heterologous gene expression in maize," *Plant Mol. Biol.*, 15(6):913-920, 1990.
McElroy et al., "Isolation of an efficient actin promoter for use in rice transformation," *Plant Cell*, 2:163-171, 1990.
Rose et al., "Introns act post-transcriptionally to increase expression of the *Arabidopsis thaliana* tryptophan pathway gene PAT1," *Plant J.*, 11(3):455-464, 1997.
Schunmann et al., "Characterization of promoter expression paterns derived from the Pht1 phosphate transporter genes of barley (*Hordeum vulgare* L.)," *J. of Exp. Bot.*, 55(398):855-865, 2004.

(Continued)

*Primary Examiner* — Phuong Bui
(74) *Attorney, Agent, or Firm* — Dentons US LLP; Carine M. Doyle Esq.

(57) ABSTRACT

The present invention relates to a method of using a dicot intron or elements thereof to enhance transgene expression in plants. The present invention also provides constructs, transgenic plants and seeds containing the polynucleotide useful for expressing transgene in plants.

3 Claims, 2 Drawing Sheets

(56) References Cited

OTHER PUBLICATIONS

Sinibaldi et al., In: Progress in Nucleic Acid Research and Molecular Biology, vol. 42, Cohn et al. eds, Academic Press, New York, NY, pp. 229-257, 1992.

Snowden et al., "Intron position affects expression from the tpi promoter in rice," *Plant Mol. Biol.*, 31(3):689-692, 1996.

Vitale et al., "Multiple conserved 5' elements are required for high-level pollen expression of the *Arabidopsis* reproductive actin *ACT1*," *Plant Mol. Biol.*, 52(6):1135-1151, 2003.

Wang et al., "Control of plant trichome development by a cotton fiber MYB gene," *The Plant Cell*, 16:2323-2334, 2004.

Xu et al., "Systemic induction of a potato pin2 promoter by wounding, methyl jasmonate, and abscisic acid in transgenic rice plants," *Plant Mol. Biol.*, 22(4):573-588, 1993.

Zou et al., "Characterization of a rice pollen-specific gene and its expression," *Am. J. of Botany*, 81(5):552-561, 1994.

* cited by examiner

US 8,673,631 B2

CHIMERIC REGULATORY SEQUENCES COMPRISING INTRONS FOR PLANT GENE EXPRESSION

CROSS REFERENCE TO RELATED APPLICATION

This application is a divisional of U.S. application Ser. No. 11/706,684, filed Feb. 15, 2007, now abandoned, the disclosure of which is herein incorporated by reference in its entirety, which application claims the benefit of priority to U.S. Provisional Application Ser. No. 60/774,700, filed on Feb. 17, 2006.

FIELD OF THE INVENTION

The invention relates to the field of plant molecular biology and plant genetic engineering and polynucleotide molecules useful for control of gene expression in plants.

BACKGROUND OF THE INVENTION

Plant genetic engineering has revolutionized agriculture and the way that we use biological systems to generate products for our use. Through transformation and the subsequent regeneration of transgenic plants, a series of agronomically important characteristics or traits have been introduced into domesticated crops. These characteristics or traits include resistance to insects, fungal disease, and other pests and disease-causing agents, tolerance to herbicides, enhanced stability or shelf-life, increased yield, environmental tolerances, and nutritional enhancements.

The success of plant genetic engineering depends on manipulation of gene expression in plants. In one approach, expression of a novel gene that is not normally expressed in a particular plant or plant tissue may confer a desired phenotypic effect. In another approach, transcription of a gene or part of a gene in an antisense orientation may produce a desirable trait by preventing or inhibiting expression of an endogenous gene. The newly introduced genetic elements are collectively referred to as transgenes. A typical transgene comprises, from 5'- to 3'-end, a regulatory sequence, a full or partial coding region in sense or antisense orientation, and often a terminator region. Many variables affect the final expression pattern of the transgene, including, for example, the insertion site of the transgene in the plant genome, the strength and specificity of the regulatory sequence, preferred codon usage in the targeted plant species, and the presence of cryptic splice sites or cryptic poly A sites. However, a reproducible expression pattern of the trans gene is achievable using technologies disclosed herein and elsewhere. The expression pattern of a transgene relates to its being transcribed efficiently at the right time during plant growth and development (temporal expression pattern), in the optimal location in the plant (spatial expression pattern), and in the amount necessary to produce the desired effect. For example, constitutive expression of a gene product may be beneficial in one location of the plant but less beneficial in another part of the plant. In other cases, it may be beneficial to have a gene product produced at a certain developmental stage of the plant or in response to certain environmental or chemical stimuli.

The commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant that each gene is modulated or controlled for the desired expression and that the regulatory elements are diverse in order to reduce the potential of gene silencing. In light of these and other considerations, it is apparent that optimal control of gene expression and regulatory element diversity are important in plant biotechnology.

SUMMARY OF THE INVENTION

The present invention relates to modulating plant gene expression with a chimeric regulatory sequence comprising a promoter and a selected dicot intron or sequence motif of a dicot intron that enhances and/or expands the expression pattern of a transgene when compared to that achievable by the promoter alone.

Accordingly, one embodiment of the invention is to provide a method of enhancing transgene expression in a dicot plant using a chimeric DNA regulatory sequence comprising an intron derived from a dicot species and a monocot promoter. The chimeric regulatory sequence is fused to a structural gene within a DNA plant expression construct for modulating the expression of the structural gene in a plant cell. When compared to a corresponding transgene comprising the monocot promoter but lacking the dicot intron, the transgene comprising the chimeric regulatory sequence exhibits an enhanced and broadened expression pattern.

Another embodiment of the invention is to provide a method to enhance the expression of a transgene comprising a nucleotide sequence encoding a glyphosate tolerance protein. When the nucleotide sequence encoding a glyphosate tolerance protein is operably linked to a chimeric regulatory sequence in accordance with the invention, the expression of the transgene can provide both vegetative and reproductive tissue tolerance in transgenic plants.

According to another embodiment, chimeric DNA regulatory sequences are provided that comprise a monocot promoter and a dicot intron. Transgenes comprising such chimeric regulatory sequences are also provided. According to a specific embodiment, the transgene is one comprising the chimeric regulatory sequence and a nucleotide sequence encoding a glyphosate tolerance protein.

According to yet another embodiment, a method is provided for identifying novel regulatory elements for enhancing transgene expression comprising the steps of testing the efficacy of a plurality of dicot introns in broadening the spatial expression pattern of the transgene, and identifying a unique motif in the dicot introns conferring such a broadening effect. Also provided is a method for regulating gene expression in plants comprising the steps of constructing a recombinant enhancer containing the unique motif and operably linking the recombinant enhancer with a promoter in a transgene to enable a broadened spatial expression pattern of the transgene. The recombinant enhancer can be placed within a heterologous promoter or upstream or downstream of the promoter, and in the forward or reverse direction.

According to yet another embodiment of the invention, a recombinant enhancer is provided comprising at least one copy of an identified motif (SEQ ID NO:17), which enhancer is capable of enhancing gene expression in male reproductive tissue of plants. Recombinant enhancers containing two, three, or four copies of the unique motif are also provided.

According to another embodiment of the invention, a recombinant enhancer is provided which comprises SEQ ID NO:17 and at least two other motifs selected from the group consisting of SEQ ID NOs:18, 19, and 20.

According to another embodiment of the invention, DNA constructs comprising recombinant enhancers described above are provided. Such DNA constructs can be useful in expressing genes of interest in plants, including, but not limited to, genes that confer herbicide tolerance, insect control, disease resistance, increased stability or shelf-life, higher yield, nutritional enhancement, expression of pharmaceutical or other desired polypeptide product, or a desirable change in plant physiology or morphology, and so on.

In other embodiments of the invention, transgenic plants are provided that are transformed with a DNA construct comprising a recombinant enhancer.

BRIEF DESCRIPTION OF THE SEQUENCE LISTING

Figure 1:
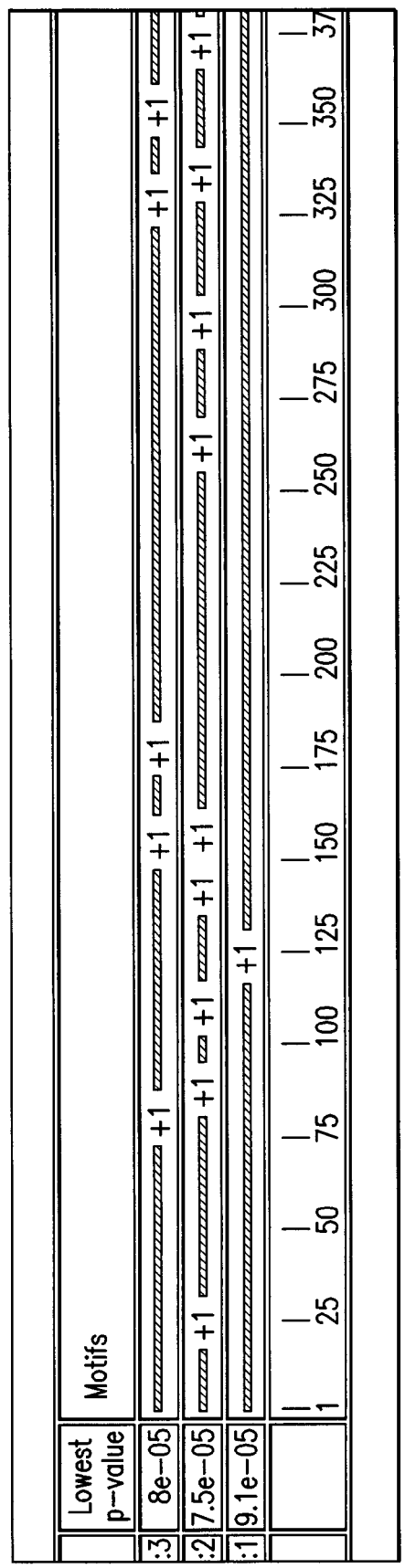
FIG. 1 is a diagram of motif occurrence in introns At-iEF1α (1), At-iANT1 (2), and At-iAct7 (3). Each shaded box with the indication "+1" represents one motif. Base numbers of the intron sequence are indicated on the bottom of the graph.

SEQ ID NO:1 is a forward PCR primer used for isolation of the rice TPI promoter.
SEQ ID NO:2 is a reverse PCR primer used for isolation of the rice TPI promoter.
SEQ ID NO:3 is another reverse PCR primer used for isolation of the rice TPI promoter.
SEQ ID NO:4 is another forward PCR primer used for isolation of the rice TPI promoter.
SEQ ID NO:5 is a forward PCR primer used for isolation of the intron At-iEF1β.
SEQ ID NO:6 is a reverse PCR primer used for isolation of the intron At-iEF1β.
SEQ ID NO:7 is a forward PCR primer used for isolation of the intron At-iANT1.
SEQ ID NO:8 is a reverse PCR primer used for isolation of the intron At-iANT1.
SEQ ID NO:9 is a forward PCR primer used for isolation of the intron At-iEF1α.
SEQ ID NO:10 is a reverse PCR primer used for isolation of the intron At-iEF1α.
SEQ ID NO:11 is a forward PCR primer used for isolation of the intron Nt-ieIF4A10.
SEQ ID NO:12 is a reverse PCR primer used for isolation of the intron Nt-ieIF4A10.
SEQ ID NO:13 is a forward PCR primer used for isolation of the intron At-iAct7.
SEQ ID NO:14 is a reverse PCR primer used for isolation of the intron At-iAct7.
SEQ ID NO:15 is a forward PCR primer used for isolation of the intron At-iASP.
SEQ ID NO:16 is a reverse PCR primer used for isolation of the intron At-iASP.
SEQ ID NO:17 is the nucleic acid sequence of a motif identified from dicot introns capable of enhancing male reproductive tissue expression of transgenes.
SEQ ID NO:18 is the nucleic acid sequence of a Fac109 motif.
SEQ ID NO:19 is the nucleic acid sequence of a Fac029 motif.
SEQ ID NO:20 is the nucleic acid sequence of a PHO2 motif.
SEQ ID NO:21 is the nucleic acid sequence of chimeric regulatory sequence Os-pTPI-L::At-iEF1α.
SEQ ID NO:22 is the nucleic acid sequence of chimeric regulatory sequence Os-pTPI-S::At-iEF1α.
SEQ ID NO:23 is the nucleic acid sequence of chimeric regulatory sequence FMV::At-iEF1α.
SEQ ID NO: 24 is the nucleic acid sequence of chimeric regulatory sequence FMV::At-iEF1β.
SEQ ID NO:25 is the nucleic acid sequence of chimeric regulatory sequence FMV::Nt-ieIF4A10.
SEQ ID NO:26 is the nucleic acid sequence of chimeric regulatory sequence FMV::At-iASP.
SEQ ID NO:27 is the nucleic acid sequence of chimeric regulatory sequence FMV::At-iANT1.
SEQ ID NO:28 is the nucleic acid sequence of chimeric regulatory sequence FMV::At-iAct7.

DETAILED DESCRIPTION OF THE INVENTION

The following detailed description is provided to better define the present invention and to guide those of ordinary skill in the art in the practice of the present invention. Unless otherwise noted, terms are to be understood according to conventional usage by those of ordinary skill in the relevant art.

The invention disclosed herein provides methods and compositions for regulating transgene expression in plants. Specifically, introns isolated from a dicot species (also referred to hereinafter as dicot intron) can be used to enhance transgene expression in a dicot plant. A chimeric DNA regulatory sequence is provided comprising a dicot intron and a monocot promoter. Methods of using such regulatory sequences in enhancing transgene expression are also provided. The present invention also relates to a method of identifying unique motifs from a class of introns having similar broadening effect on the spatial expression pattern of a transgene. A recombinant enhancer comprising such a identified unique motif (SEQ ID NO:17) is provided, which can be used in a recombinant DNA construct to enable transgene expression in male reproductive tissue of plants. The design, construction, and use of recombinant enhancers comprising elements of dicot introns are objects of this invention.

Introns are intervening sequences present in the pre-mRNA but absent in the mature RNA following excision by a precise splicing mechanism. The ability of natural introns to enhance gene expression has been known in various organisms, including mammals (Buchman and Berg (1988) Mol Cell Bio 8: 4395-4405; Chung and Perry (1989) Mol Cell Biol 9: 2075-2082), insects (Meredith and Storti (1993) Dev Biol 159: 500-512), nematodes (Okkema et al. (1993) Genetics 135: 385-404) and plants (Callis et al. (1987) Genes Dev 1: 1183-1200; Luehrsen and Walbot (1991) Mol Gen Genet 225: 81-93; Rose and Last (1997) Plant J 11: 455-464; Wang et al. (2004) Plant Cell 16: 2323-2334). The mechanism of such intron-mediated enhancement (IME), however, is not well understood. Evidence has accumulated to suggest that after transcription, monocot introns can increase the level of mRNA by enhancing the maturation and stability of nascent transcripts (Callis et al. (1987) Genes Dev 1: 1183-1200;

Mascarenhas et al. (1990) Plant Mol Biol 15: 913-920; Clancy et al. (1994) Plant Sci 98: 151-161). In this respect, the enhancing effect of monocot introns is different from transcriptional enhancers, which is independent of position and orientation (Callis et al. (1987) Genes Dev 1: 1183-1200; Snowden et al. (1996) Plant Mol Biol 31: 689-692). IME by dicot introns may be effected via a different mechanism from that of monocot introns. For example, some dicot introns have been shown to behave like transcriptional enhancers (Vitale et al. (2003) Plant Mol Biol 52: 1135-1151; Wang et al. (2004) Plant Cell 16: 2323-2334).

A transcriptional enhancer, as used herein, means a cis-acting transcriptional regulatory element, which confers on an organism an aspect of the overall control of gene expression. An enhancer may function to bind transcription factors, trans-acting protein factors that regulate transcription. The transcriptional enhancers may be embedded in a promoter region and can be identified by a number of techniques, including deletion analysis, i.e. deleting one or more nucleotides from the 5' end of internal to a promoter; DNA binding protein analysis using DNase I footprinting, methylation interference, in vivo genomic footprinting by ligation-mediated PCR, and other conventional assays; or by DNA sequence similarity analysis with known cis-acting elements by conventional DNA sequence comparison methods. Once identified, an enhancer can be placed upstream or downstream of a heterologous promoter sequence to enhance gene expression, irrespective of the enhancer orientation. A heterologous sequence is a sequence which originates from a foreign source or species or, if from the same source, is modified from its original form. A promoter is a polynucleotide molecule that is involved in recognition and binding of RNA polymerase II and other proteins (trans-acting transcription factors) to initiate transcription. A plant promoter is a native or non-native promoter that is functional in plant cells. A plant promoter can be used as a 5' regulatory sequence for modulating expression of an operably linked gene or genes. The effect of plant promoters on the genes they control may be described by their temporal, spatial, or developmental expression patterns.

Many commonly utilized monocot promoters have retained the first intron for maximal promoter activity. These include, for example, maize alcohol dehydrogenase 1 (Adh1) (Dennis et al. (1984) Nucleic Acid Res 12: 3983-4000; Callis et al. (1987) Genes Dev 1: 1183-1200), maize polyubiquitin 1 (ubi1) (Christensen et al. (1992) Plant Mol Biol 18: 675-689; Christensen and Quail (1996) Transgenic Res 5: 213-218), maize shrunken-1 (Mass et al. (1991) Plant Mol Biol 16: 199-207) and rice actin (McElroy et al. (1990) Plant Cell 2: 163-171). The role of the introns in enhancing gene expression in monocots is believed to be facilitating intron splicing in nascent RNAs. This theory is supported by the following examples. Large internal deletions of the first intron of the maize Adh1 gene that strongly reduced splicing also impaired the expression-enhancing effect of this intron (Luehrsen and Walbot (1994) Plant Mol Biol 24: 449-463). Similarly, when the maize Hsp82 intron was rendered unspliceable by a point mutation at the 5' or 3' splice site, the ability of that intron to enhance expression was also lost (Sinibaldi and Mettler (1992) In W E Cohn, K Moldave, eds, Progress in Nucleic Acid Research and Molecular Biology, Vol 42. Academic Press, New York, pp 229-257).

Recently, promoters derived from some dicot species have also been reported to require the retention of the first intron for enhanced tissue specific gene expression (Vitale et al. (2003) Plant Mol Biol 52: 1135-1151; Wang et al. (2004) Plant Cell 16: 2323-2334; U.S. Pat. No. 6,660,911).

Examples of dicot introns enhancing the tissue specific activity of its native promoter include the first intron of cotton GLABARA 1 (GL1) which is necessary for the expression of GL1 in trichome cells (Wang et al. (2004) Plant Cell 16: 232-2334), intron L of *Arabidopsis* actin 1 which is required for pollen expression (Vitale et al. (2003) Plant Mol Biol 52: 1135-1151), and the first intron of *Arabidopsis* EF1α which is necessary for male reproductive tissue expression (U.S. Pat. No. 6,660,911). The role of introns in enhancing gene expression in dicot plants may be different from that in monocot plants. In dicot plants, intron splicing may not be necessary for enhancing gene expression because a dicot intron can be placed in either the reverse or forward orientation upstream of the native promoter while retaining the enhancing effect. The intron L of *Arabidopsis* actin 1 exemplifies such an enhancer (Vitale et al. (2003) Plant Mol Biol 52: 1135-1151).

The phenomenon of IME has also been observed in certain situations where a promoter is fused with a heterologous intron to drive the expression of a transgene. In monocot plants, for example, the inclusion of the maize Adh1 intron to the barley HvPht1;1 or HvPht1;2 promoter enhanced gene expression approximately 20-fold, but did not appear to affect the tissue specificity of the expression (Schunmann et al. (2004) J Exp Bot 55: 855-865). Transgene expression in rice is also enhanced using a chimeric regulatory sequence comprising the rice actin 1 intron and the potato pin 2 promoter (Xu et al. (1993) Plant Mol Biol 22: 573-5880). In dicot plants, transgene expression is enhanced, for example, by a chimeric regulatory sequence comprising the first intron of *Arabidopsis* EF1α and the Figwort mosaic virus (FMV) promoter (U.S. Pat. No. 6,660,911). However, there has been no report to date on the composition and use of a chimeric regulatory sequence comprising a monocot promoter and a dicot intron in enhancing transgene expression in a dicot plant.

According to one embodiment of the invention, a chimeric regulatory sequence comprising a dicot intron and a monocot promoter is provided. Such chimeric regulatory sequence is used to drive transgene expression in a dicot plant wherein enhanced level of expression of the transgene is obtained. The chimeric regulatory sequence also enables the expression of the transgene in a tissue where there is little or no expression of the transgene lacking the dicot intron.

The chimeric regulatory sequence provided herein can be used to modulate the expression of an operably linked gene or genes of interest. As used herein, the term "operably linked" or "fused" refers to a first polynucleotide molecule connected with a second polynucleotide molecule, where the polynucleotide molecules are so arranged that the first polynucleotide molecule affects a desired function of the second polynucleotide molecule. The term "chimeric", as used herein, refers to a product of the fusion of portions of two or more different polynucleotide molecules. As used herein, the term "chimeric regulatory sequence" refers to a sequence capable of modulating gene expression in plants, which is produced through the manipulation of known promoters or other polynucleotide molecules such as an intron. Thus, the design, construction, and use of chimeric regulatory sequences according to the methods disclosed herein for modulating the expression of operably linked polynucleotide sequences are encompassed by the present invention.

DNA sequence motifs from dicot intron sequences can be identified and these motifs often play significant roles in enhancing gene expression. For example, by searching a plant cis-acting regulatory DNA elements (PLACE) database, a MYB binding motif is identified from the first introns of cotton GaMYB2, GLABARA1, and WEREWOLF, which are regulators of trichome (cotton fiber) development. The mutagenesis of this motif greatly weakens the trichome expression of the affected gene and trichome formation is inhibited (Wang et al. (2004) Plant Cell 16: 232-2334). Other methods may also be employed to identify sequence motifs important for dicot intron function in enhancing gene expression, for example, deletional analysis and a position-dependent scoring matrix program for motif searching.

Thus, according to an embodiment of the invention, a method for identifying novel regulatory elements from dicot introns is provided wherein a plurality of chimeric sequences comprising dicot introns are tested for efficacy in broadening transgene expression pattern in a dicot plant and a unique motif is identified from dicot introns capable of conferring such a broadening effect on the transgene expression pattern. A de novo approach is employed to search for a previously unknown motif that occurs in the efficacious dicot intron sequences but not in the non-efficacious sequences. Any program designed for motif searching can have utility in the present invention. Sequence analysis programs designed for motif searching can be used for identification of cis elements. Preferred computer programs would include but are not limited to MEME, SIGNAL SCAN, and GENESCAN. MEME is a program that identifies conserved motifs (either nucleic acid or peptide) in a group of unaligned sequences. MEME saves these motifs as a set of profiles. These profiles can then be used to search a database of subject sequences. A MEME algorithm (version 2.2) can be found in version 10.0 of the GCG package (Bailey and Elkan, Machine Learning, 21(1-2):51-80, 1995).

A motif thus identified and shown to be important in broadening transgene expression pattern can be used to construct novel, highly efficient transcription enhancers capable of driving or enhancing transgene expression in plant tissues. These enhancers, referred to hereinafter as recombinant enhancers, encompass recombinant polynucleotide molecules comprising the identified motif or advantageously less than the full length sequence of the dicot intron from which the motif is identified. A "recombinant" nucleic acid is made by an artful combination of two or more otherwise separated segments of naturally occurring nucleic acid sequence(s), e.g., by chemical synthesis of a designed molecule or by the manipulation of isolated segments of nucleic acids by genetic engineering techniques.

Another approach to identify motifs important for broadening transgene expression pattern in a dicot plant is to search efficacious dicot intron sequences for known transcription factor binding motifs that are absent in non-efficacious dicot intron sequences. Any motif searching software package, for example, PromoterScan, could be used to search a given input DNA sequence for known transcription factor binding motifs. The motifs thus identified can be used to construct recombinant enhancers or other chimeric regulatory elements.

Any number of methods well known to those skilled in the art can be used to isolate the intron or fragments of an intron to be used as disclosed herein. For example, polymerase chain reaction (PCR) can be used to amplify intron sequences using primers designed based on publicly available sequence information. Nucleic acid fragments can also be obtained by other techniques such as by directly synthesizing the fragment by chemical means, as is commonly practiced by using an automated oligonucleotide synthesizer. Those of skill in the art are familiar with the standard resource materials that describe specific conditions and procedures for the construction, manipulation, and isolation of macromolecules (e.g. polynucleotide molecules, plasmids), as well as the generation of recombinant organisms and the screening and isolation of polynucleotide molecules.

The copy number and spacing of an identified intron motif in a recombinant enhancer can be manipulated to achieve desired levels of expression in plant tissues. It is to be noted that the identified intron motif can be oriented in a recombinant enhancer in either the forward or reverse direction. When desirable, one copy of the identified motif could be used to recombine with another segment of polynucleotide sequence to form a novel enhancer. Alternatively, two or more copies of the same motif can be used in a recombinant enhancer to have increased transcriptional enhancing activity. For example, two, three, four or five copies of an identified motif can be placed in tandem in a recombinant enhancer. The distance between two adjacent motifs can be 0, 10, 50, 100, 200, 300, 500, and 1000 bases. Optimally, the distance between two adjacent motifs is between 10 to 250 bases. A recombinant enhancer thus constructed can be used in a recombinant DNA construct to drive transgene expression.

As used herein, the term "recombinant DNA construct", "recombinant construct" or "expression construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner. Methods are known for introducing constructs into a cell in such a manner that a transcribable polynucleotide molecule is transcribed into a functional mRNA molecule that is translated and therefore expressed as a protein product. Constructs may also be made to be capable of expressing antisense RNA molecules, in order to inhibit translation of a specific RNA molecule of interest. For the practice of the present invention, conventional compositions and methods for preparing and using constructs and host cells are well known to one skilled in the art, see for example, Molecular Cloning: A Laboratory Manual, 3$^{rd}$ edition Volumes 1, 2, and 3. J. F. Sambrook, D. W. Russell, and N. Irwin, Cold Spring Harbor Laboratory Press, 2000.

In one embodiment of the invention, the recombinant enhancer or chimeric regulatory sequence of the present invention is operably linked to a transcribable polynucleotide molecule that is a gene of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. For example, glyphosate tolerance can be conferred by genes including, but not limited to, *Agrobacterium* strain CP4 glyphosate resistant EPSPS gene (aroA:CP4), glyphosate oxidoreductase, and glyphosate acetyltransferase. Other desirable agronomic traits conferred by a transgene include, but not limited to, increased yield (U.S. Pat. No. 5,716,837), insect control (U.S. Pat. No. 6,063,597; U.S. Pat. No. 6,063,756; U.S. Pat. No. 6,093,695; U.S. Pat. No. 5,942,664; and U.S. Pat. No. 6,110,464), fungal disease resistance (U.S. Pat. No. 5,516,671; U.S. Pat. No. 5,773,696; U.S. Pat. No. 6,121,436; U.S. Pat. No. 6,316,407, and U.S. Pat. No. 6,506,962), virus resistance (U.S. Pat. No. 5,304,730 and U.S. Pat. No. 6,013,864), nematode resistance (U.S. Pat. No. 6,228,992), bacterial disease resistance (U.S. Pat. No. 5,516,671), starch production (U.S. Pat. No. 5,750,876 and U.S. Pat. No. 6,476,295), modified oils production (U.S. Pat. No. 6,444,876), high oil production (U.S. Pat. No. 5,608,149 and U.S. Pat. No. 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. No. 5,985,605 and U.S. Pat. No. 6,171,640), biopolymers (U.S. Pat. No. 5,958,745 and US Patent Publication No. US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700). The genetic elements, methods, and transgenes described in the patents listed above are hereby incorporated by reference.

Alternatively, a transcribable polynucleotide molecule can effect the above mentioned phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a chimeric regulatory sequence of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865; *Agrobacterium*-mediated transformation as illustrated in U.S. Pat. No. 5,824,877; U.S. Pat. No. 5,591,616; U.S. Pat. No. 5,981,840; and U.S. Pat. No. 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including *indica* and *japonica* varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

In one embodiment of the invention, a greenhouse or field evaluation for glyphosate tolerance is conducted for the transformed plants. The term "glyphosate" is used herein to refer collectively to the parent herbicide N-phosphonomethylglycine (otherwise known as glyphosate acid), to a salt or ester thereof, or to a compound which is converted to N-phosphonomethylglycine in plant tissues or which otherwise provides N-phosphonomethylglycine in ionic form (otherwise known as glyphosate ion). Illustratively, water-soluble glyphosate salts useful herein are disclosed in U.S. Pat. Nos. 3,799,758 and 4,405,531 to Franz, the disclosure of which is incorporated herein by reference.

Examples of commercial formulations of glyphosate include, without restriction, those sold by Monsanto Company as ROUNDUP®, ROUNDUP® ULTRA, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEO-FORCE, which contains glyphosate as its sodium salt; and that sold by Zeneca Limited as TOUCHDOWN® herbicide, which contains glyphosate as its trimethylsulfonium salt. The selection of application rates for a glyphosate formulation that are biologically effective is within the skill of the ordinary agricultural technician. One of skill in the art will likewise recognize that individual plant conditions, weather conditions and growing conditions can affect the results achieved in practicing the process of the present invention. Over two decades of glyphosate use and published studies relating to such use have provided abundant information from which a weed control practitioner can select glyphosate application rates that are herbicidally effective on particular species at particular growth stages in particular environmental conditions.

In one embodiment, a glyphosate-containing herbicide is applied to the plant comprising the DNA constructs of the present invention, and the plants are evaluated for the glyphosate herbicide. Any formulation of glyphosate can be used for testing plants comprising the DNA constructs of the present invention. For example, a glyphosate composition such as Roundup® Ultra can be used. The testing parameters for an evaluation of the glyphosate tolerance of the plant will vary depending on a number of factors. Factors would include, but are not limited to the type of glyphosate formulation, the concentration and amount of glyphosate used in the formulation, the type of plant, the plant developmental stage during the time of the application, environmental conditions, the application method, and the number of times a particular formulation is applied. For example, plants can be tested in a greenhouse environment using a spray application method. The testing range using Roundup® Ultra can include, but is not limited to 8 oz/acre to 256 oz/acre. The preferred commercially effective range can be from 16 oz/acre to 64 oz/acre of Roundup® Ultra, depending on the crop and stage of plant development. A crop can be sprayed with at least one application of a glyphosate formulation. For testing in cotton an application of 32 oz/acre at the 3-leaf stage may be followed by additional applications at later stages in development. For wheat an application of 32 oz/acre of Roundup® Ultra at the 3-5 leaf stage can be used and may be followed with a pre- or post-harvest application, depending on the type of wheat to be tested. The test parameters can be optimized for each crop in order to find the particular plant comprising the constructs of the present invention that confers the desired commercially effective glyphosate tolerance level.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

This example illustrates that a chimeric regulatory sequence comprising a monocot promoter and a dicot intron can enhance transgene expression in a dicot plant. Specifically, the rice cytosolic triosephosphate isomerase (TPI) promoter was fused with a dicot intron At-iEF1α to form a chimeric regulatory sequence. This chimeric regulatory sequence provided increased transgene expression in vegetative tissues of a dicot plant and also expression in reproductive tissue where TPI promoter alone is not active.

The assembly of the chimeric regulatory sequences and plant expression constructs is as follows. A long version (Os-pTPI-L) and a short version (Os-pTPI-S) of the rice TPI promoter were amplified using primers designed based on the sequence of Genbank Accession Number L04967 as described in Xu et al. (1993) Plant Mol Biol 22: 573-588 and rice genomic DNA as template. The reaction mixture for the PCR was set up as follows: 0.5 µg template DNA, 25 pmole of each primer, Taq polymerase (BMB, Indianapolis, Ind.) using wax beads for "hot start" PCR. The PCR thermocycler conditions were as follows: 94° C. for one minute; 30 cycles of: 92° C. for 40 seconds, 55° C. for one minute, 72° C. for one minute and 30 seconds; and a five minute 72° C. extension. The PCR reaction was purified using GeneClean II (Bio101 Inc., Vista, Calif.), digested with appropriate restriction enzymes and ligated into constructs digested with the same or compatible restriction enzymes. The assembly of the chimeric regulatory sequences and plant expression constructs was achieved by inserting an amplified rice TPI promoter into pMON71535, a plant transformation-ready pBI121 based plasmid, which contained At-iEF1α operably linked to CTP2-aroA:CP4. As a control, an amplified rice TPI promoter was also inserted into a similar construct, pMON65322, which lacked At-iEF1α. The presence of CTP2-aroA:CP4 allowed assessment of the activity of the regulatory sequences by spray application of glyphosate (Roundup Ultra™). A more detailed description of construct assembly follows:

Rice TPI promoter PCR products generated with SEQ ID NOs: 1 and 2 were digested with Not I and Hind III and ligated to pMON71535 previously digested with the same enzymes to form pMON65380. This construct contained the Os-pTPI-L operably linked to CTP2-aroA:CP4. The PCR products generated with SEQ ID NOs: 1 and 3 were digested with Not I and Pci I and ligated to pMON65322 previously digested with Not I and Nco I to form pMON65381. It should be noted that restriction enzymes Pci I and Nco I produce compatible ends on their respective DNA substrates. The resulting construct contained the chimeric regulatory sequence (Os-pTPI-L::At-iEF1α; SEQ ID NO:21) operably linked to CTP2-aroA:CP4. Similarly, the PCR products generated with SEQ ID Nos: 4 and 2 were digested with Not I and Hind III and ligated to pMON71535 previously digested with the same enzymes to form pMON65382. The resulting construct contained the Os-pTPI-S operably linked to CTP2-aroA:CP4. Finally, PCR products generated with SEQ ID NOs: 4 and 3 were digested with Not I and Pci I and ligated to pMON65322 previously digested with Not I and Nco I to form pMON65383. This construct contained the chimeric regulatory sequence, Os-pTPI-S::At-iEF1α (SEQ ID NO:22), operably linked to CTP2-aroA:CP4.

The efficacy of the chimeric regulatory sequence comprising a dicot intron (At-iEF1α) and a monocot promoter (Os-pTPI) in driving expression of the CTP2-aroA:CP4 was compared with that of regulatory sequences lacking a dicot intron in transgenic *Arabidopsis thaliana*. The transgenic *Arabidopsis thaliana* plants were produced by the vacuum infiltration method (Beclitold et al. (1992) C R Acad Paris Life Sci 316: 1194-1199). Harvested seeds were cast in soil in trays in a growth chamber adjusted for 24° C. and 16-hour photoperiod cycle to permit normal growth and development of the plants. Initial screening of glyphosate tolerant transgenic *Arabidopsis* seedlings was carried out by spray application of the herbicide glyphosate (Roundup® Ultra) at a rate of 24 ounces/acre. The surviving plants were transplanted into individual pots. Each surviving plant represented a distinct transgenic event. At flowering (approx. 16 days after bolting), plants were sprayed a second time with glyphosate at rates of 24 ounces/acre and 128 ounces/acre to determine the efficacy of the different constructs for conferring reproductive tolerance. The reproductive tolerance to glyphosate in *Arabidopsis* was measured by the percent of plants (events) producing siliques that contained seeds. The vegetative tolerance of the plants to glyphosate was also monitored following the second application. The vegetative tolerance to glyphosate in *Arabidopsis* was measured by the percent of plants (events) showing no injury of the vegetative tissues (complete vegetative tolerance). Results of the effect of various constructs on the vegetative and reproductive tolerance in *Arabidopsis* are shown in Table I.

TABLE 1

The effect of EF1a intron on activity of rice TPI promoter in *Arabidopsis*

| vector | | | | # of lines tested | Tolerant Events | |
|---|---|---|---|---|---|---|
| pMON | Promoter | Intron | Glyphosate Treatment | | Vegetative % | Reproductive % |
| 65380 | Os-pTPI-L* | — | 24 oz/A | 30 | 57 | 0 |
| | | | 128 oz/A | 29 | 31 | 0 |
| 65381 | Os-pTPI-L | At-iEF1α | 24 oz/A | 30 | 93 | 50 |
| | | | 128 oz/A | 30 | 83 | 43 |
| 65382 | Os-pTPI-S** | — | 24 oz/A | 38 | 79 | 0 |
| | | | 128 oz/A | 30 | 47 | 0 |
| 65383 | Os-pTPI-S | At-iEF1α | 24 oz/A | 58 | 88 | 50 |
| | | | 128 oz/A | 26 | 77 | 42 |

*L = Long,
**S = Short

Data in Table 1 indicated that the dicot intron At-iEF1α was conferring reproductive tissue glyphosate tolerance in *Arabidopsis*. Transgenic plants containing only the promoter Os-pTPI-L or Os-pTPI-S showed various degrees of vegetative tolerance depending on the application rate of glyphosate. These transgenic plants, however, failed to yield seeds and exhibited no reproductive tolerance. The introduction of the dicot intron At-iEF1α into the regulatory sequence induced reproductive tissue tolerance to glyphosate in more than 40% of the transgenic plants tested. The remainder of the plants failed to produce seed. An increase in vegetative tolerance was also observed in transgenic plants comprising the rice TPI promoter and At-iEF1α intron.

This example illustrates that a dicot intron can be used in a chimeric regulatory sequence to enhance transgene expression and broaden the spatial expression pattern of a monocot promoter in dicot plants. Specifically, the dicot intron was shown to enhance transgene expression in vegetative tissues of a dicot plant and enable reproductive tissue expression of the trans gene. The enhanced transgene expression was manifested by the increased glyphosate tolerance in the subject tissues.

Example 2

This example illustrates that not all dicot introns are capable of broadening the spatial expression pattern of a heterologous promoter, and that introns can be selected for use in chimeric regulatory sequences comprising a heterologous promoter to achieve a broader spatial expression pattern than that of the promoter alone. In this example, the Figwort Mosaic Virus 35S promoter (FMV promoter) was fused with different dicot introns to form various chimeric regulatory sequences to test the tissue specific enhancing effect of the introns.

Different chimeric regulatory sequences and expression constructs containing such regulatory sequences were prepared as follows. The FMV promoter as described in U.S. Pat. No. 6,018,100 (herein incorporated by reference in its entirety) was fused with the first native intron of *Arabidopsis* elongation factor 1α (At-iEF1α), the first native intron from the coding region of *Arabidopsis* elongation factor 1β (At-iEF1β), the first intron of *N. tabaccum* initiation factor 4A10 (Nt-ieIF4A10), the first native intron and 5' leader from *Arabidopsis* aspartic proteinase like protein (At-iASP), the first native intron from *Arabidopsis* adenylate translocator protein (At-iANT1), and the first native intron from *Arabidopsis* actin 7 protein (At-iAct7), respectively, to form chimeric regulatory sequences SEQ ID NOs:23-28. pMON81508, a plant transformation-ready plasmid based on pBI121, was used as a control wherein the FMV promoter was fused directly to the coding region of the CTP2-aroA:CP4 EPSPS.

All introns were cloned separately into the Bgl II site situated between the promoter and the coding sequence. Specifically, At-iEF1β intron was amplified from *Arabidopsis* genomic DNA using SEQ ID NO:5 (forward primer) and SEQ ID NO:6 (reverse primer). PCR conditions were as described in Example 2. The resulting PCR products were digested with Bgl II and inserted directionally into a pMON81508 digested with Bgl II to form pMON81518. At-iANT1 was amplified from *Arabidopsis* genomic DNA using SEQ ID NO:7 (forward primer) and SEQ ID NO:8 (reverse primer), digested with Sin I (which produced compatible ends to Bgl II digested products), and ligated to a Bgl II digested pMON81508. The resulting construct was designated pMON81522. At-iEF1α was amplified from *Arabidopsis* genomic DNA using SEQ ID NO:9 (forward primer) and SEQ ID NO:10 (reverse primer), digested with Bgl II, and ligated to a Bgl II digested pMON81508 to form pMON81531. Nt-ieIF4A10 was amplified from tobacco genomic DNA using SEQ ID NO:11 (forward primer) and SEQ ID NO:12 (reverse primer), digested with Bgl II, and ligated to a Bgl II digested pMON81508 to form pMON81532. At-iAct7 was amplified from *Arabidopsis* genomic DNA using SEQ ID NO:13 (forward primer) and SEQ ID NO:14 (reverse primer), digested with Sin I, and ligated to a Bgl II digested pMON81508 to form pMON81533. Finally At-iASP was amplified from *Arabidopsis* genomic DNA using SEQ ID NO:15 (forward primer) and SEQ ID NO:16 (reverse primer), digested with Bgl II, and ligated to a Bgl II digested pMON81508 to form pMON81534.

Transgenic *Arabidopsis* plants were generated with the constructs described above following the protocol disclosed in Example 1. Reproductive tolerance of the transgenic plants to glyphosate was measured by the percent of plants (events) producing siliques that contained seeds. The results are shown in Table 2.

TABLE 2

Performance of plants transformed with vectors containing different introns inserted into FMV: CP4 EPSPS expression cassette.

| Vector | | # of lines tested | Arabidopsis Reproductive Tolerance % | # of lines tested | Arabidopsis Reproductive Tolerance % |
|---|---|---|---|---|---|
| pMON | Intron | 24 oz/A | | 128 oz/A | |
| 81508 | No intron | 10 | 0 | 11 | 0 |
| 81518 | At-iEF1β | 30 | 0 | 20 | 0 |
| 81522 | At-iANT1 | 28 | 61 | 25 | 48 |
| 81531 | At-iEF1 α | 27 | 22 | 9 | 22 |
| 81532 | Nt-ieIF4A10 | 40 | 0 | 29 | 0 |
| 81533 | At-iAct7 | 32 | 59 | 30 | 43 |
| 81534 | At-iASP | 26 | 0 | 25 | 0 |

Data in Table 2 indicate that not all dicot introns can expand the spatial expression pattern of the FMV promoter to the male reproductive tissue. For example, At-iEF1β, Nt-ieIF4A10, and At-iASP failed to confer reproductive tolerance to transgenic *Arabidopsis*. The dicot intron At-iANT1 showed the highest efficacy in conferring reproductive tolerance to transgenic *Arabidopsis* in both the 24 ounce/acre and 128 ounce/acre of glyphosate applications. The dicot intron At-iAct7 showed slightly lower efficacy and At-iEF1α had the lowest efficacy amongst the three introns that enabled transgenic *Arabidopsis* to yield seeds.

This example shows that dicot introns can be selected as tissue specific enhancers, which can broaden the spatial expression pattern of a transgene comprising the selected intron and a heterologous promoter.

Example 3

This example illustrates the identification of motifs unique to a class of tissue specific enhancers. Specifically, unique sequence motifs were identified from the three dicot introns conferring male reproductive tissue expression in transgenic *Arabidopsis* described in Example 2.

Computational analysis was performed to identify unique motifs that were present only in the identified introns that exerted tissue specific enhancement of gene expression. MEME is a tool to uncover one or more motifs in a collection of DNA sequences (Bailey and Elkon (1994) In: Proceedings of the Second International Conference on Intelligent Systems for Molecular Biology, Standford, Calif., AAAI Press, Bethesda, Md., pp 28-36). MEME takes advantage of expectation maximization to fit a two-component finite mixture model to the set of selected sequences. As described, the processes for motif identification are to fit a mixture model to the sequence data, to probabilistically erase the occurrences of the motif thus found, and to repeat the process for identifying successive motifs.

MEME analysis was applied to sequences of the three introns (At-iEF1α of pMON81531, At-iANT1 of pMON81522, and At-iAct7 of pMON81533). The sequence motif T/CAGATCTG (SEQ ID NO:17) was identified in all three introns. The occurrence of the identified motif in the intron sequence is diagrammed in FIG. 1.

Results of Examples 2 and 3 indicate that the copy number of the identified motif in each intron is correlated with the degree of efficacy of the intron in enabling tissue specific gene expression. At-iEF1α had the lowest efficacy and had only one copy of the identified motif. At-iAct7 had five copies of the identified motif and had slightly lower efficacy than that of At-iANT1, which had 9 copies of this motif. The results showed a significant increase in efficacy when the copy number of this motif increased from 1 (as in At-iEF1α) to 5 (as in At-iAct7). Further increase in copy number from 5 (as in At-iAct7) to 9 (as in At-iANT1) showed only a slight increase in efficacy, indicating that the cumulative effect of multiple copies of the motif was starting to plateau when the copy number approached 9 and the effect of each additional copy might decline at higher copy numbers.

The identified motif (SEQ ID NO:17) was absent in the three introns that were shown to be ineffective in inducing male reproductive tissue gene expression in Example 2. The absence or presence of the identified motif was reflected in the E-value associated with each intron. The E-value of a sequence was the expected number of sequences in a random database of the same size that would match the motifs as well as the sequence did and was equal to the combined p-value of the sequence times the number of sequences in the database. The p-value of a sequence measured the strength of the match of the sequence to all the motifs. To derive the E-value, a position-dependent scoring matrix was generated from the 15 motifs of the three effective introns and the scoring matrix was then applied to the three effective introns and the three ineffective introns. The scoring matrix was as follows:

"ALPHABET=ACGT log-odds matrix: alength=4 w=8

| 0.000218 | 0.199982 | 0.000115 | 0.799685 |
|---|---|---|---|
| 0.333329 | 0.399849 | 0.066738 | 0.200084 |
| 0.000218 | 0.000115 | 0.999449 | 0.000218 |
| 0.999551 | 0.000115 | 0.000115 | 0.000218 |
| 0.000218 | 0.000115 | 0.000115 | 0.999551 |
| 0.000218 | 0.999449 | 0.000115 | 0.000218 |
| 0.000218 | 0.066738 | 0.000115 | 0.932929 |
| 0.000218 | 0.000115 | 0.999449 | 0.000218" |

The E values for At-iANT1, At-iAct7 and At-iEF1α were 0.0161, 0.0147, and 0.14, respectively. In comparison, the E values for At-iASP, Nt-ieIF4A10, and At-iEF1β were 0.663, 0.863, and 0.71, respectively. These significantly higher E values were indicative of the absence of the identified motif in the later group of introns.

Example 4

The significance of the identified motif in introns and promoter sequences that confer male reproductive tissue specific expression was confirmed with the promoter and intron L of *Arabidopsis* actin 1. The intron L and a 55-bp conserved domain within the promoter have been shown to be effective for the pollen specific gene expression in *Arabidopsis* (Vitale et al. (2003) Plant Mol Biol 52: 1135-1151). The same scoring matrix in Example 3 was employed in the MEME program to search for the presence of the motif on the sequences. Two motifs corresponding to the previously identified motif (SEQ ID NO:17) were found between the nucleotides 89 and 117 of intron L. The calculated E value for intron L was 0.011 indicating the presence of the motif (SEQ ID NO:17). Additionally, the identified motif was present in tandem in the center of the reverse strand of the 55-bp conserved domain of the act1 promoter. The presence of the identified motif in elements essential for pollen specific expression signifies the importance of the identified motif in conferring tissue specific expression.

Example 5

Figure 2:
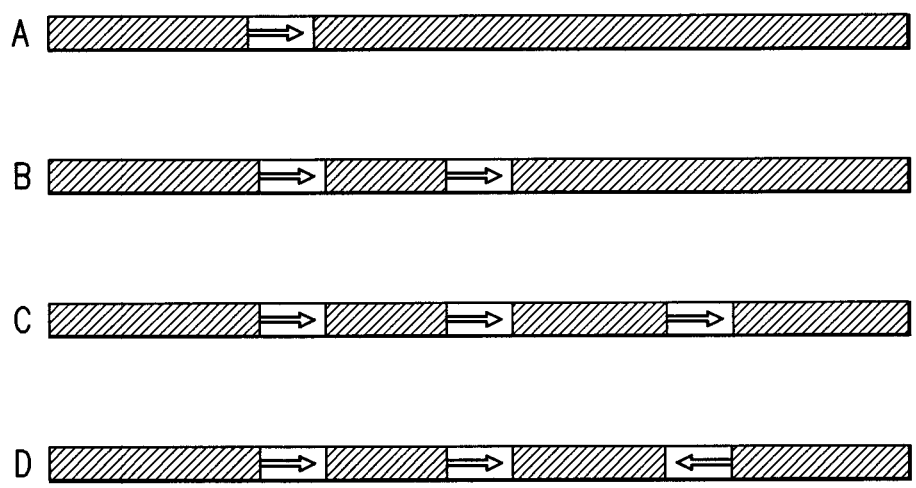
FIG. 2 is a schematic representation of modification of the intron At-iEF1α. A is the native intron with one copy of the motif SEQ ID NO:17 (indicated by a blank box with an arrow showing the direction of the motif sequence); B is a modified At-iEF1α with an extra copy of the motif inserted approx. 100 bp downstream from the original motif; C is a modified At-iEF1α with two extra motifs inserted approximately 100 bp and 200 bp, respectively, downstream from the original motif, wherein all motifs are in the forward direction; D is a modified At-iEF1α with two extra motifs inserted approx. 100 bp and 200 bp, respectively, downstream from the original motif, wherein one inserted motif is in the reverse direction.

This example illustrates the use of the identified motif in constructing recombinant enhancers for transgene expression. To enhance the expression of CP4 EPSPS in *Arabidopsis* and especially in the male reproductive tissue, a recombinant enhancer can be constructed comprising the intron At-iEF1α and at least one more copy of the identified motif (SEQ ID NO:17). The technical methods of introducing the motif at designated sites on the nucleotide sequence of the intron are known to those of skill in the art. For example, site-directed mutagenesis can be performed to add or delete single or stretches of nucleotides to alter the nucleotide sequence of a native intron. The intron At-iEF1α is a relatively inefficient enhancer because it contains only a single copy of the motif (SEQ ID NO:17). As shown in FIG. 2, the native intron (A) can be modified to have two (B) or three (C and D) copies of the motif. The introduced motif can be placed in a reverse direction (D) within the recombinant enhancer. The recombinant enhancers thus constructed can be tested in expression constructs by operably linking to a promoter such as the FMV promoter and a coding region such as the CTP2:CP4 EPSPS. The expression constructs can then be introduced into *Arabidopsis* by transformation and the transformed plants are sprayed with glyphosate at the appropriate developmental stage. Transgenic plants can be scored for reproductive tolerance to glyphosate. A recombinant enhancer with increasing copy number of the identified motif can show higher efficacy in enhancing tissue specific gene expression, which can be evidenced by the production of siliques containing seeds despite of glyphosate spray application.

Example 6

This example illustrates the identification of additional motifs that may affect the enhancer activity of a dicot intron. Specifically, known cis-acting regulatory DNA elements are identified from the three dicot introns conferring male reproductive tissue expression in transgenic *Arabidopsis* described in Example 2.

Dicot intron sequences from Example 2 were searched against a collection of known transcription factor binding motifs compiled from the databases of PLACE, PlantCARE, and Transfac. This collection of known motifs contains only motifs identified from plant, yeast, and fungal sources. The program PromoterScan was used for the search and three motifs, Fac109, Fac029, and PHO2, were identified from the sequences of the introns At-iANT1, At-iEF1α, and At-iAct7. The motif Fac109 was originally reported as a cis-acting motif of *Arabidopsis thaliana* histone H4 promoter (Chaubet et al. (1996) Plant J 10: 425-35) and was found in At-iANT1 with 3 copies and in At-iAct7 with 2 copies. The motif Fac029 was reported to be an element of the bean PAL2 promoter responsible for the vascular-specific gene expression (Hatton et al. (1995) Plant J 7: 859-76). One copy of Fac029 was found in At-iAct7 and At-iEF1α, respectively. The motif PHO2 was a cis-acting element of the HIS4 promoter of PHO2 yeast (Brazas and Stillman (1993) Mol Cell Biol 13: 5524-37) and was found here in two copies in each of introns At-iEF1α, and At-iANT1. None of the motifs Fac109, Fac029 and PHO2 was found in the three introns that were ineffective in conferring male reproductive tissue gene expression in Example 2. The number and relative position of these elements could play a role in enhancer activity of the introns At-iAct7, At-iANT1, and At-iEF1α. Additionally, these elements (SEQ ID NOs: 18-20) can act synergistically with the motif SEQ ID NO: 17 in a recombinant enhancer to achieve optimal levels of gene expression in plant tissue.

One of skill in the art will appreciate that, by modifying the order of the motifs, the number of the motifs, and/or the length of the space between the motifs (SEQ ID NOs:17-20), one can construct a recombinant enhancer with desired enhancer activity. However, in each case, the recombinant enhancer will retain the activity of driving gene expression in male reproductive tissue of plants.

Having illustrated and described the principles of the present invention, it should be apparent to persons skilled in the art that the invention can be modified in arrangement and detail without departing from such principles. We herein claim all modifications that are within the spirit and scope of the appended claims.

All publications and published patent documents cited in the specification are incorporated herein by reference to the same extent as if each individual publication or patent application was specifically and individually indicated to be incorporated by reference.

We claim:

1. A chimeric DNA regulatory sequence comprising a monocot promoter operably linked to a dicot intron, wherein said chimeric DNA regulatory sequence provides enhanced transgene expression in dicot plants relative to a regulatory sequence comprising a monocot promoter without a dicot intron, wherein said dicot intron is the first intron of At-Act7 and said monocot promoter is the rice TPI promoter.

2. The chimeric DNA regulatory sequence of claim 1, further comprising a sequence encoding a glyphosate tolerance protein.

3. The chimeric DNA regulatory sequence of claim 2, wherein said glyphosate tolerance protein is selected from the group consisting of glyphosate oxidoreductase, glyphosate acetyltransferase, and 5-enolpyruvyl-3-phosphoshikimate synthase.

* * * * *

SEQUENCE LISTING

<160> NUMBER OF SEQ ID NOS: 28

<210> SEQ ID NO 1
<211> LENGTH: 34
<212> TYPE: DNA
<213> ORGANISM: Artificial sequence
<220> FEATURE:
<223> OTHER INFORMATION: synthetic sequence

<400> SEQUENCE: 1
gaactagaag cggccgctag ttgttgagtc cact                    34

<210> SEQ ID NO 2
<211> LENGTH: 25
<212> TYPE: DNA
<213> ORGANISM: Artificial sequence
<220> FEATURE:

-continued

<223> OTHER INFORMATION: synthetic sequence

<400> SEQUENCE: 2
gcaagcttgg gagcagaggt gtggc                                          25

<210> SEQ ID NO 3
<211> LENGTH: 33
<212> TYPE: DNA
<213> ORGANISM: Artificial sequence
<220> FEATURE:
<223> OTHER INFORMATION: synthetic sequence

<400> SEQUENCE: 3
gcaattacat gtttgccacc aacgaagaac ttg                                 33

<210> SEQ ID NO 4
<211> LENGTH: 37
<212> TYPE: DNA
<213> ORGANISM: Artificial sequence
<220> FEATURE:
<223> OTHER INFORMATION: synthetic sequence

<400> SEQUENCE: 4
gaactagaag cggccgcacg taaggatcca aatgtta                             37

<210> SEQ ID NO 5
<211> LENGTH: 30
<212> TYPE: DNA
<213> ORGANISM: Artificial sequence
<220> FEATURE:
<223> OTHER INFORMATION: synthetic sequence

<400> SEQUENCE: 5
gcagatctgg gttagaatct gttttctaag                                     30

<210> SEQ ID NO 6
<211> LENGTH: 28
<212> TYPE: DNA
<213> ORGANISM: Artificial sequence
<220> FEATURE:
<223> OTHER INFORMATION: synthetic sequence

<400> SEQUENCE: 6
cgagatctgt acctataaac atacatac                                       28

<210> SEQ ID NO 7
<211> LENGTH: 31
<212> TYPE: DNA
<213> ORGANISM: Artificial sequence
<220> FEATURE:
<223> OTHER INFORMATION: synthetic sequence

<400> SEQUENCE: 7
gcggatcctt aggtatgact cgtttctctc a                                   31

<210> SEQ ID NO 8
<211> LENGTH: 31
<212> TYPE: DNA
<213> ORGANISM: Artificial sequence
<220> FEATURE:
<223> OTHER INFORMATION: synthetic sequence

<400> SEQUENCE: 8
cgggatccgt gaactctgca aaatcacata a                                   31

<210> SEQ ID NO 9

```
<211> LENGTH: 34
<212> TYPE: DNA
<213> ORGANISM: Artificial sequence
<220> FEATURE:
<223> OTHER INFORMATION: synthetic sequence

<400> SEQUENCE: 9
gcagatctct gaggtaagcg ttaacgtacc ctta                              34

<210> SEQ ID NO 10
<211> LENGTH: 32
<212> TYPE: DNA
<213> ORGANISM: Artificial sequence
<220> FEATURE:
<223> OTHER INFORMATION: synthetic sequence

<400> SEQUENCE: 10
gcagatctgt caacaaatct gcaaaaaaaa ga                                32

<210> SEQ ID NO 11
<211> LENGTH: 28
<212> TYPE: DNA
<213> ORGANISM: Artificial sequence
<220> FEATURE:
<223> OTHER INFORMATION: synthetic sequence

<400> SEQUENCE: 11
tcagatcttt tcctcatctc tatcaggt                                     28

<210> SEQ ID NO 12
<211> LENGTH: 29
<212> TYPE: DNA
<213> ORGANISM: Artificial sequence
<220> FEATURE:
<223> OTHER INFORMATION: synthetic sequence

<400> SEQUENCE: 12
gcagatctaa cctgtagcaa ataaaagaa                                    29

<210> SEQ ID NO 13
<211> LENGTH: 31
<212> TYPE: DNA
<213> ORGANISM: Artificial sequence
<220> FEATURE:
<223> OTHER INFORMATION: synthetic sequence

<400> SEQUENCE: 13
tcggatcctc aaggtgagtc tctagatccg t                                 31

<210> SEQ ID NO 14
<211> LENGTH: 32
<212> TYPE: DNA
<213> ORGANISM: Artificial sequence
<220> FEATURE:
<223> OTHER INFORMATION: synthetic sequence

<400> SEQUENCE: 14
ctggatcctt cactaaaaaa aaagtaaaat ga                                32

<210> SEQ ID NO 15
<211> LENGTH: 31
<212> TYPE: DNA
<213> ORGANISM: Artificial sequence
<220> FEATURE:
<223> OTHER INFORMATION: synthetic sequence

<400> SEQUENCE: 15
```

```
gcagatctttt ggtgagctct ctttcttatg a                                    31
```

<210> SEQ ID NO 16
<211> LENGTH: 31
<212> TYPE: DNA
<213> ORGANISM: Artificial sequence
<220> FEATURE:
<223> OTHER INFORMATION: synthetic sequence

<400> SEQUENCE: 16

```
cgagatctgt acctattcat tgacaacaaa a                                     31
```

<210> SEQ ID NO 17
<211> LENGTH: 8
<212> TYPE: DNA
<213> ORGANISM: Arabidopsis thaliana
<220> FEATURE:
<221> NAME/KEY: misc_feature
<222> LOCATION: (1)..(1)
<223> OTHER INFORMATION: n is c or t

<400> SEQUENCE: 17

```
nagatctg                                                                8
```

<210> SEQ ID NO 18
<211> LENGTH: 9
<212> TYPE: DNA
<213> ORGANISM: Arabidopsis thaliana

<400> SEQUENCE: 18

```
agatcgacg                                                               9
```

<210> SEQ ID NO 19
<211> LENGTH: 12
<212> TYPE: DNA
<213> ORGANISM: Arabidopsis thaliana

<400> SEQUENCE: 19

```
ccaccaaccc cc                                                          12
```

<210> SEQ ID NO 20
<211> LENGTH: 9
<212> TYPE: DNA
<213> ORGANISM: Arabidopsis thaliana

<400> SEQUENCE: 20

```
caatttaaa                                                               9
```

<210> SEQ ID NO 21
<211> LENGTH: 3241
<212> TYPE: DNA
<213> ORGANISM: Artificial sequence
<220> FEATURE:
<223> OTHER INFORMATION: synthetic sequence
<220> FEATURE:
<223> OTHER INFORMATION: rice TPI promoter=1-2511
<220> FEATURE:
<223> OTHER INFORMATION: Arabidopsis EF1a 5'non-coding region
      polynucleotide=2512-2620,3221-3241
<220> FEATURE:
<223> OTHER INFORMATION: Arabidopsis EF1a intron=2621-3220

<400> SEQUENCE: 21

```
gctagttgtt gagtccacta tagactctta aataggccat gttagagaaa aacgatagtt       60
ctgtaaaggc cggctttctg atcgtctctc tactagtaat acgcaataat taaattcttg      120
tagcaagtgc catgattttc tacattttgg atctaaatac gtgactttc ttgtagatgg      180
```

```
actatacaac ggccgttgct tatctcgtct gctcttgttt ttctcgttgt gagccggtgt    240
caggctgatg gcatgcaaaa catccctgca tgcatcttcc ttcttggttc tttctcttcc    300
acatcatcaa atttgtttac ataataataa atagagcgca tcttccttct ttgtttcttt    360
ctcttccaca tcatcaaatt tatttactta acaataaata gagcccattg attaatacct    420
ttgtacatgc ccttacgcgg gaaggaatcg acgacaatgg tgcgcatgga ccaacgtggc    480
tatacatcag cgacgacaac tcacaaccgc gaagcaatgt aaacgcagta gcatctaaat    540
aggtaacgac aaagatgttc actaatctcc aatttgtagt ttgtagctag tagcatatca    600
tcccagacgg gcatatcgcg gttataaata accagcgatg gtccaattag tttgtccaat    660
tactttcacg agttaatccc gatcattcca ggattaatat atagcaggtg cacaatacac    720
atcggtctca aacggccttc cttttagaca actaattata caagagatat gtaattaatt    780
aggtgaaccc atcgatcaaa agcatcacga ccttacctat agagctaaag cctccaatgg    840
cgagagagtt ggtgagtaaa gagcagatga cacagaacgc atatgtacac atgattgttt    900
cttctagacg atggtctttc ctggcttgaa taatgatgtt ttatagtagt attccactaa    960
taattaataa atatccctag ttggtcatct tcccgacgac taagcggtca acctaagcac   1020
tcaacagcta ctagtactaa tgaatgtcga tctgcatgtg cttcctgatg tgacactaat   1080
gattgattaa tttaagacta tatgatgttg aagattgaac cacccaaatt ctctacccat   1140
ttatatttat tccctaatac aatgaagcat gcatttattt ctagactaga gacatttaat   1200
tattttgcca ctcttaaatg tggtaagtaa ccatttacca tgtataccca catgtcatag   1260
acacgtaagg atccaaatgt taacacatag gtgtcagata gttaaacgtc taacctaaaa   1320
gtaacaaata tttaaatatc ccttatatct atgattgaaa ggaaaaaagt ctaagtacaa   1380
ttgtcgagat atggcaggtt tggtaggtct ctaacttctc aacttaactc aaataattaa   1440
gtttagagtg gaattatgga gcaccttgaa tccagattca tctctctaat ttgttttaat   1500
agcactgctc tactcccttt tagatggaat tgaaatcgtt tggttggact tcatccctaa   1560
cctccataag aggtgaaatt ggagctaaa gtatgtcaaa catggccata taatctaaga    1620
acagcttatc gagatatcca acaaaaaata atcgttctcc tatttcagtg agtaaaaacc   1680
tgatggtcca aacgagttgg gctgaaaatg ggacagtgtt tcggtgagac gggcccagca   1740
agaacatagg cctggttggg cccctattcc ccctacgttt tctcggccca cccaccgttg   1800
ggctcggctc gggcctacca tcgggcggag aggaggccca actcgggaaa aaggagaaac   1860
agaaaagagg ccgaaaaggc gaaagggatc gatgaggtgg ggaccaccgg accagcgaga   1920
gatgcgcatc ccgatgcagc acgatgccgc ggcgccctct gttccgctcc gcgccgcggc   1980
cacgaaaacc acgacgccgc cgggatcatc tgcgtccgcc ttaccagtgg ccgtcgctgc   2040
tatggatgac ttaagcagtt tttttttatgt gtataaataa aacagggtag ttaacgagtc   2100
atactttggt tctggaagag aatatctttt taggaaaaaa gcaataggtc atcttactct   2160
ttgctacagg tgcaataatt tgcccggaca atagacctga gtatagttta tttagttcta   2220
aacaatgcat cagaatatgg aggaaaaaga tggccttagt ataggatcaa ttgagatgta   2280
cagttaaaca aaaaagtaga tatgagttta caaaattgat gcggaatatt atatccatgt   2340
agtagctccc atgtactagt ttcttttgct tgaaaaaata aaagaagcag ataatttcta   2400
gagaagtcca gagaataaaa agattggtgg tgggagtggg acccacctgt cattgtcgga   2460
ggagcctgcc tcgcctcatg tgatcccatc ggaggccaca cctctgctcc caagcttggt   2520
ttcggattca acgctataaa taaaaccact ctcgttgctg attccattta tcgttcttat   2580
```

```
tgaccctagc cgctacacac ttttctgcga tatctctgag gtaagcgtta acgtacccct    2640
agatcgttct ttttctttt cgtctgctga tcgttgctca tattatttcg atgattgttg    2700
gattcgatgc tctttgttga ttgatcgttc tgaaaattct gatctgttgt ttagatttta    2760
tcgattgtta atatcaacgt ttcactactt ctaaacgata atttattcat gaaactattt    2820
tcccattctg atcgatcttg ttttgagatt ttaatttgtt cgattgattg ttggttggtg    2880
gatctatata cgagtgaact tgttgatttg cgtatttaag atgtatgtcg atttgaattg    2940
tgattgggta attctggagt agcataacaa atccagtgtt ccctttttct aagggtaatt    3000
ctcggattgt ttgctttata tctcttgaaa ttgccgattt gattgaattt agctcgctta    3060
gctcagatga tagagcacca caattttgt ggtagaaatc ggtttgactc cgatagcggc    3120
tttttactat gattgttttg tgttaaagat gattttcata atggttatat atgtctactg    3180
tttttattga ttcaatattt gattgttctt ttttttgcag atttgttgac agtctctaac    3240
c                                                                    3241
```

<210> SEQ ID NO 22
<211> LENGTH: 1979
<212> TYPE: DNA
<213> ORGANISM: Artificial sequence
<220> FEATURE:
<223> OTHER INFORMATION: synthetic sequence
<220> FEATURE:
<223> OTHER INFORMATION: rice TPI promoter=1-1250
<220> FEATURE:
<223> OTHER INFORMATION: Arabidopsis EF1a 5' non-coding region
      polynucleotide=1251-1359,1960-1980
<220> FEATURE:
<223> OTHER INFORMATION: Arabidopsis EF1a intron=EF1a 1360-1959

<400> SEQUENCE: 22

```
cacgtaagga tccaaatgtt aacacatagg tgtcagatag ttaaacgtct aacctaaaag      60
taacaaatat ttaaatatcc cttatatcta tgattgaaag gaaaaaagtc taagtacaat     120
tgtcgagata tggcaggttt ggtaggtctc taacttctca acttaactca ataattaag     180 tttagagtgg aattatggag caccttgaat ccagattcat ctctctaatt tgttttaata     240
gcactgctct actccctttt agatggaatt gaaatcgttt ggttggactt catccctaac     300
ctccataaga ggtgaaattg gagctagaag tatgtcaaac atggccatat aatctaagaa     360
cagcttatcg agatatccaa caaaaaataa tcgttctcct atttcagtga gtaaaaacct     420
gatggtccaa acgagttggg ctgaaaatgg gacagtgttt cggtgagacg ggcccagcaa     480
gaacataggc ctggttgggc ccctattccc cctacgtttt ctcggcccac ccaccgttgg     540
gctcggctcg ggcctaccat cgggcggaga ggagggcccaa ctcgggaaaa aggagaaaca     600
gaaaagaggc cgaaaaggcg aaagggatcg atgaggtggg gaccaccgga ccagcgagag     660
atgcgcatcc cgatgcagca cgatgccgcg gcgccctctg ttccgctccg cgccgcggcc     720
acgaaaacca cgacgccgcc gggatcatct gcgtccgcct taccagtggc cgtcgctgct     780
atggatgact taagcagttt ttttatgtg tataaataaa acagggtagt taacgagtca     840
tactttggtt ctggaagaga atatctttt aggaaaaag caataggtca tcttactctt     900
tgctacaggt gcaataattt gcccggacaa tagacctgag tatagtttat ttagttctaa     960
acaatgcatc agaatatgga ggaaaaagat ggccttagta taggatcaat tgagatgtac    1020
agttaaacaa aaaagtagat atggatttac aaaattgatg cggaatatta tatccatgta    1080
gtagctccca tgtactagtt tcttttgctt gaaaaaataa aagaagcaga taatttctag    1140
```

```
agaagtccag agaataaaaa gattggtggt gggagtggga cccacctgtc attgtcggag    1200
gagcctgcct cgcctcatgt gatcccatcg gaggccacac ctctgctccc aagcttggtt    1260
tcggattcaa cgctataaat aaaaccactc tcgttgctga ttccatttat cgttcttatt    1320
gaccctagcc gctacacact tttctgcgat atctctgagg taagcgttaa cgtacccttaa   1380 gatcgttctt tttcttttc gtctgctgat cgttgctcat attatttcga tgattgttgg    1440
attcgatgct ctttgttgat tgatcgttct gaaaattctg atctgttgtt tagattttat    1500
cgattgttaa tatcaacgtt tcactacttc taaacgataa tttattcatg aaactatttt    1560
cccattctga tcgatcttgt tttgagattt taatttgttc gattgattgt tggttggtgg    1620
atctatatac gagtgaactt gttgatttgc gtatttaaga tgtatgtcga tttgaattgt    1680
gattgggtaa ttctggagta gcataacaaa tccagtgttc ccttttttcta agggtaattc    1740 tcggattgtt tgctttatat ctcttgaaat tgccgatttg attgaattta gctcgcttag    1800
ctcagatgat agagcaccac aattttttgtg gtagaaatcg gtttgactcc gatagcggct    1860
ttttactatg attgttttgt gttaaagatg atttttcataa tggttatata tgtctactgt    1920
ttttattgat tcaatatttg attgttcttt tttttgcaga tttgttgaca gtctctaac    1979

<210> SEQ ID NO 23
<211> LENGTH: 1275
<212> TYPE: DNA
<213> ORGANISM: Artificial sequence
<220> FEATURE:
<223> OTHER INFORMATION: synthetic sequence
<220> FEATURE:
<223> OTHER INFORMATION: FMV promoter=1-552
<220> FEATURE:
<223> OTHER INFORMATION: Petunia Hsp70 leader=553-645
<220> FEATURE:
<223> OTHER INFORMATION: Arabidopsis EF1a intron with flanking
      sequence=646-1275

<400> SEQUENCE: 23
gcattccaga ttgggttcaa tcaacaaggt acgagccata tcactttatt caaattggta     60
tcgccaaaac caagaaggaa ctcccatcct caaaggtttg taaggaagaa ttctcagtcc    120
aaagcctcaa caaggtcagg gtacagagtc tccaaaccat tagccaaaag ctacaggaga    180
tcaatgaaga atcttcaatc aaagtaaact actgttccag cacatgcatc atggtcagta    240
agtttcagaa aaagacatcc accgaagact taaagttagt gggcatcttt gaaagtaatc    300
ttgtcaacat cgagcagctg gcttgtgggg accagacaaa aaaggaatgg tgcagaattg    360
ttaggcgcac ctaccaaaag catctttgcc tttattgcaa agataaagca gattcctcta    420
gtacaagtgg ggaacaaaat aacgtggaaa agagctgtcc tgacagccca ctcactaatg    480
cgtatgacga acgcagtgac gaccacaaaa gaattccctc tatataagaa ggcattcatt    540
cccatttgaa ggacacagaa aaatttgcta cattgtttca caaacttcaa atattattca    600
tttatttgtc agctttcaaa ctctttgttt cttgtttgtt gattgagatc tctgaggtaa    660
gcgttaacgt acccttagat cgttcttttt cttttttcgtc tgctgatcgt tgctcatatt    720
atttcgatga ttgttggatt cgatgctctt tgttgattga tcgttctgaa aattctgatc    780
tgttgtttag attttatcga ttgttaatat caacgtttca ctacttctaa acgataattt    840
attcatgaaa ctattttccc attctgatcg atcttgtttt gagattttaa tttgttcgat    900
tgattgttgg ttggtggatc tatatacgag tgaacttgtt gatttgcgta tttaagatgt    960
atgtcgattt gaattgtgat tgggtaattc tggagtagca taacaaatcc agtgttccct    1020
ttttctaagg gtaattctcg gattgtttgc tttatatctc ttgaaattgc cgatttgatt    1080
```

```
gaatttagct cgcttagctc agatgataga gcaccacaat ttttgtggta gaaatcggtt    1140
tgactccgat agcggctttt tactatgatt gttttgtgtt aaagatgatt ttcataatgg    1200
ttatatatgt ctactgtttt tattgattca atatttgatt gttctttttt ttgcagattt    1260
gttgacagat ctatc                                                     1275

<210> SEQ ID NO 24
<211> LENGTH: 770
<212> TYPE: DNA
<213> ORGANISM: Artificial sequence
<220> FEATURE:
<223> OTHER INFORMATION: synthetic sequence
<220> FEATURE:
<223> OTHER INFORMATION: FMV promoter=1-552
<220> FEATURE:
<223> OTHER INFORMATION: Petunia Hsp70 leader=553-645
<220> FEATURE:
<223> OTHER INFORMATION: Arabidopsis EF1b intron with flanking
      sequence=646-770

<400> SEQUENCE: 24
gcattccaga ttgggttcaa tcaacaaggt acgagccata tcactttatt caaattggta     60
tcgccaaaac caagaaggaa ctcccatcct caaaggtttg taaggaagaa ttctcagtcc    120
aaagcctcaa caaggtcagg gtacagagtc tccaaaccat tagccaaaag ctacaggaga    180
tcaatgaaga atcttcaatc aaagtaaact actgttccag cacatgcatc atggtcagta    240
agtttcagaa aaagacatcc accgaagact taaagttagt gggcatcttt gaaagtaatc    300
ttgtcaacat cgagcagctg gcttgtgggg accagacaaa aaaggaatgg tgcagaattg    360
ttaggcgcac ctaccaaaag catctttgcc tttattgcaa agataaagca gattcctcta    420
gtacaagtgg ggaacaaaat aacgtggaaa agagctgtcc tgacagccca ctcactaatg    480
cgtatgacga acgcagtgac gaccacaaaa gaattccctc tatataagaa ggcattcatt    540
cccatttgaa ggacacagaa aaatttgcta cattgtttca caaacttcaa atattattca    600
tttatttgtc agctttcaaa ctctttgttt cttgtttgtt gattgagatc tgggttagaa    660
tctgttttct aagggctgtc tcaattatct atcttgtttt gaaacaatag tagtaaccat    720
tactttcttc tgtctctcta tgtatgtatg tttataggta cagatctatc                770

<210> SEQ ID NO 25
<211> LENGTH: 1574
<212> TYPE: DNA
<213> ORGANISM: Artificial sequence
<220> FEATURE:
<223> OTHER INFORMATION: synthetic sequence
<220> FEATURE:
<223> OTHER INFORMATION: FMV promoter=1-552
<220> FEATURE:
<223> OTHER INFORMATION: Petunia Hsp70 leader=553-645
<220> FEATURE:
<223> OTHER INFORMATION: tobacco eIF4A10 intron with flanking
      sequence=646-1663

<400> SEQUENCE: 25
gcattccaga ttgggttcaa tcaacaaggt acgagccata tcactttatt caaattggta     60
tcgccaaaac caagaaggaa ctcccatcct caaaggtttg taaggaagaa ttctcagtcc    120
aaagcctcaa caaggtcagg gtacagagtc tccaaaccat tagccaaaag ctacaggaga    180
tcaatgaaga atcttcaatc aaagtaaact actgttccag cacatgcatc atggtcagta    240
agtttcagaa aaagacatcc accgaagact taaagttagt gggcatcttt gaaagtaatc    300
ttgtcaacat cgagcagctg gcttgtgggg accagacaaa aaaggaatgg tgcagaattg    360
```

```
ttaggcgcac ctaccaaaag catctttgcc tttattgcaa agataaagca gattcctcta    420
gtacaagtgg ggaacaaaat aacgtggaaa agagctgtcc tgacagccca ctcactaatg    480
cgtatgacga acgcagtgac gaccacaaaa gaattccctc tatataagaa ggcattcatt    540
cccatttgaa ggacacagaa aaatttgcta cattgtttca caacttcaa atattattca     600 tttatttgtc agctttcaaa ctctttgttt cttgtttgtt gattgagatc ttttcctcat    660
ctctatcagg ttagctatgt ttttttccc tttaatattt taatgtattt cttgtaatat     720
ttgtttgtgt attgaagatt gaatcttgat gattgattgt tggtctgact acagctgggt    780
tttgtgttat gtaactattt ttaactattt tggatagagg tctgtttgat gtgatgttct    840
tgattataaa aataccatcc tactttgtta tctcatatct ggttggaaca tgagcaattt    900
catttctcct agttcttgaa ttaaaaacct gaaagtattg tgcaaaaaga tgctaggaat    960
gagactatca ttgttttgat gcaatatgtt cttttaagta ataggtgttt tgtaagaagt   1020
ctacgcagtt ctggatgtat tttactactc gggaaaactg gatagttgga tacttattat   1080
gtataggaag taaatgtggg gattataatg cctttctctg ccatctgctc tttgtatttt   1140
gtgtaaagct tggcatgcct ctcgtcagat agccatcgct accgtacatt cttttaagaa   1200
tgaagcactt agacacttgc tcgtttctgc ctttgtcaca ttgacccagc atcatataat   1260
ctgaaagatt ggttagcagt tggctgctat ttaacttgta tgttaaaaca attgattttc   1320
atgtgtatct cctccttttg tgctttgtgc ttcttcataa agaaagaaa acatacattc    1380 ggttgtgctc tcctcctttt tcaatggtag agaggaagaa cagataattt tattgctgct   1440
gtaggtattt gacatctgtg atattttcat agtaaggttt tgttttttcc tttttattta   1500
gttcaagatt gtttcatgaa tttccataag cgtaatacca tagttctttt atttgctaca   1560
ggttagatct atcc                                                     1574
```

<210> SEQ ID NO 26
<211> LENGTH: 1663
<212> TYPE: DNA
<213> ORGANISM: Artificial sequence
<220> FEATURE:
<223> OTHER INFORMATION: synthetic sequence
<220> FEATURE:
<223> OTHER INFORMATION: FMV promoter=1-552
<220> FEATURE:
<223> OTHER INFORMATION: Petunia Hsp70 leader=553-645
<220> FEATURE:
<223> OTHER INFORMATION: Arabidopsis ASP intron with flanking
      sequence=646-1574

<400> SEQUENCE: 26

```
gcattccaga ttgggttcaa tcaacaaggt acgagccata tcactttatt caaattggta     60
tcgccaaaac caagaaggaa ctcccatcct caaaggtttg taaggaagaa ttctcagtcc    120
aaagcctcaa caaggtcagg gtacagagtc tccaaaccat tagccaaaag ctacaggaga    180
tcaatgaaga atcttcaatc aaagtaaact actgttccag cacatgcatc atggtcagta    240
agtttcagaa aaagacatcc accgaagact taaagttagt gggcatcttt gaaagtaatc    300
ttgtcaacat cgagcagctg gcttgtgggg accagacaaa aaaggaatgg tgcagaattg    360
ttaggcgcac ctaccaaaag catctttgcc tttattgcaa agataaagca gattcctcta    420
gtacaagtgg ggaacaaaat aacgtggaaa agagctgtcc tgacagccca ctcactaatg    480
cgtatgacga acgcagtgac gaccacaaaa gaattccctc tatataagaa ggcattcatt    540
```

-continued

```
cccatttgaa ggacacagaa aaatttgcta cattgtttca caaacttcaa atattattca      600
tttatttgtc agctttcaaa ctctttgttt cttgtttgtt gattgagatc tttggtgagc      660
tctctttctt atgaaactta tcgattctct tctcgttgat tgtcttatac ttttagttct      720
ctgcttaatt tattgtcctt aatactcgtg gatttgttca taaatcgttt tctgagcagt      780
taggtaagag ttttgttacc gaatttcatg ttcttcgatt ttgaatctgg atgattgtat      840
gatgtgatta gtagactcgc ttagattttg tgatctgtgt atggtttgtg gctaattttg      900
gtttcatcgg tggtatgaat ttatttgggg ttttaggttt gtttgattac gtaatcggac      960
tgtttacttg aagatttatc gattatagtt gtgatcgttt ttagttgatt gagaagaaga     1020
aaataaattt catgctcttg ttattgtcgc gattgtggcg attttcagtg tcttatgaat     1080
caattatgtt gcatgtgagt cttggtgcaa ttgagattgt ttcctttttt tactagattg     1140
cttgtcttat tgaacaaaac tttccattta tgttgaaaag gtttatagga acggatgttt     1200
agggttttgt tgtaatctgg gtatttgctt tctgatttcg gcaagcaaat gtcgatttca     1260
aggtttatat cactttctct agcaaaagaa gtctttagtc atttgcaaag tcaagagagt     1320
ttttacttta tttattgctt ccacgctatt gcttcgtggc tgattgagag agaccaatta     1380
aactaataat ttgtagtttg tacaatatat tgcgtgtaac attgtccttc gttatctgtt     1440
tgaggaggag gaccgagtta gcctattttt agtcactttta caaattttct tttatgttgc     1500
atcattcaat atgaactctc tgatataaat atatgtatac atactggttg acttttatgg     1560
gtatggttct ctgctttttt tctctgtgat ggtctcttga ttctaacttt ctttgttta     1620 tgttttggt ttttgttgtc aatgaatagg tacagatcta tcc                        1663
```

<210> SEQ ID NO 27
<211> LENGTH: 1268
<212> TYPE: DNA
<213> ORGANISM: Artificial sequence
<220> FEATURE:
<223> OTHER INFORMATION: synthetic sequence
<220> FEATURE:
<223> OTHER INFORMATION: FMV promoter=1-552
<220> FEATURE:
<223> OTHER INFORMATION: Petunia Hsp70 leader=553-645
<220> FEATURE:
<223> OTHER INFORMATION: Arabidopsis ANT1 intron with flanking
      sequence=646-1268

<400> SEQUENCE: 27

```
agcattccag attgggttca atcaacaagg tacgagccat atcactttat tcaaattggt       60
atcgccaaaa ccaagaagga actcccatcc tcaaaggttt gtaaggaaga attctcagtc      120
caaagcctca acaaggtcag ggtacagagt ctccaaacca ttagccaaaa gctacaggag      180
atcaatgaag aatcttcaat caaagtaaac tactgttcca gcacatgcat catggtcagt      240
aagtttcaga aaaagacatc caccgaagac ttaaagttag tgggcatctt tgaaagtaat      300
cttgtcaaca tcgagcagct ggcttgtggg gaccagacaa aaaggaatg gtgcagaatt      360 gttaggcgca cctaccaaaa gcatctttgc ctttattgca aagataaagc agattcctct      420
agtacaagtg gggaacaaaa taacgtggaa aagagctgtc ctgacagccc actcactaat      480
gcgtatgacg aacgcagtga cgaccacaaa agaattccct ctatataaga aggcattcat      540
tcccatttga aggacacaga aaaatttgct acattgtttc acaaacttca atattattc      600 atttatttgt cagctttcaa actctttgtt tcttgtttgt tgattgagat ccttaggtat      660
gactcgtttc tctcagatct gtgattcttt ataatctcgt cgttcttcaa atcattgtta      720
```

-continued

```
tattcgtttc ttcgatctgt gtttttaga tctgtaaggt aaatgagacg tttcgatctg      780
tagatctgat tgttatattg atagattatg ttatctgctt tgcttaaagt ccgatcggaa      840
tgttttgtgc tcattgtcga atatctgatg tatcggtttc atagatctgc ttcttttgt       900
gcgtttcgtt gatctgataa tcttctagtg atcaaaatcg tttggatctg ttgactttag      960
tttaaaatgt atccgatctg atgtcgaggc ttcattattg gaagttgtta ttgttgtaat     1020
cctgatttaa gttgctgttc ttaaatttat atgatctttg cgttataata tgacatggta     1080
gatcttggtt catggttcac tgttttccaa taaacttggt ttgtttggtt ggatagcgtt     1140
ctgtgatacg accatgtctt gtgttggata agaattctct gaatttcctt ggctggtttg     1200
tagtatgtta ttcacgtctg gtttctcatc aatgattatg tgattttgca gagttcacgg     1260
atctatcc                                                              1268

<210> SEQ ID NO 28
<211> LENGTH: 1210
<212> TYPE: DNA
<213> ORGANISM: Artificial sequence
<220> FEATURE:
<223> OTHER INFORMATION: synthetic sequence
<220> FEATURE:
<223> OTHER INFORMATION: FMV promoter=1-552
<220> FEATURE:
<223> OTHER INFORMATION: Petunia Hsp70 leader=553-645
<220> FEATURE:
<223> OTHER INFORMATION: Arabidopsis Act7 intron with flanking
      sequence=646-1210

<400> SEQUENCE: 28
gcattccaga ttgggttcaa tcaacaaggt acgagccata tcactttatt caaattggta       60
tcgccaaaac caagaaggaa ctcccatcct caaaggtttg taaggaagaa ttctcagtcc      120
aaagcctcaa caaggtcagg gtacagagtc tccaaaccat tagccaaaag ctacaggaga      180
tcaatgaaga atcttcaatc aaagtaaaact actgttccag cacatgcatc atggtcagta      240
agtttcagaa aaagacatcc accgaagact taaagttagt gggcatcttt gaaagtaatc      300
ttgtcaacat cgagcagctg gcttgtgggg accagacaaa aaaggaatgg tgcagaattg      360
ttaggcgcac ctaccaaaag catctttgcc tttattgcaa agataaagca gattcctcta      420
gtacaagtgg ggaacaaaat aacgtggaaa agagctgtcc tgacagccca ctcactaatg      480
cgtatgacga acgcagtgac gaccacaaaa gaattccctc tatataagaa ggcattcatt      540
cccatttgaa ggcacagaa aaatttgcta cattgtttca caaacttcaa atattattca       600
tttatttgtc agctttcaaa ctctttgttt cttgtttgtt gattgagatc ctcaaggtga      660
gtctctagat ccgttcgctt gattttgctg ctcgttagtc gttattgttg attctctatg      720
ccgatttcgc tagatctgtt tagcatgcgt tgtggtttta tgagaaaatc tttgttttgg      780
gggttgcttg ttatgtgatt cgatccgtgc ttgttggatc gatctgagct aattcttaag      840
gtttatgtgt tagatctatg gagtttgagg attcttctcg cttctgtcga tctctcgctg      900
ttatttttgt ttttttcagt gaagtgaagt tgtttagttc gaaatgactt cgtgtatgct      960
cgattgatct ggttttaatc ttcgatctgt taggtgttga tgtttacaag tgaattctag     1020
tgttttctcg ttgagatctg tgaagtttga acctagtttt ctcaataatc aacatatgaa     1080
gcgatgtttg agtttcaata aacgctgcta atcttcgaaa ctaagttgtg atctgattcg     1140
tgtttacttc atgagcttat ccaattcatt tcggtttcat tttactttt ttttagtgaa      1200
ggatctatcc                                                            1210
```